United States Patent [19]

Deichert et al.

[11] 4,195,030

[45] Mar. 25, 1980

[54] PREPARATION OF MONOMERIC ORGANOSILICON ESTERS

[75] Inventors: William G. Deichert, Macedon, N.Y.; Kai C. Su, Arlington, Tex.; Martin F. Van Buren, Webster, N.Y.

[73] Assignee: Bausch & Lomb Incorporated, Rochester, N.Y.

[21] Appl. No.: 2,284

[22] Filed: Jan. 10, 1979

[51] Int. Cl.² .............................................. C07F 7/08
[52] U.S. Cl. ........................................... 260/448.2 E
[58] Field of Search ................................. 260/448.2 E

[56] References Cited

U.S. PATENT DOCUMENTS

| 2,906,735 | 9/1959 | Speier | 260/448.2 E X |
| 3,878,263 | 4/1975 | Martin | 260/448.2 E UX |

OTHER PUBLICATIONS

Morrison and Boyd, "Organic Chemistry", 2nd Ed., 1966, pp. 666-667.

Primary Examiner—Paul F. Shaver
Attorney, Agent, or Firm—Frank C. Parker; Ronald L. Lyons

[57] ABSTRACT

A process is disclosed which involves the preparation of monomeric organosilicon esters in a much shorter time and at a much higher purification than previously known in the art. More specifically, the process comprises reacting a cyclosilalkoxane having the general formula:

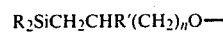

wherein R is a monovalent hydrocarbon radical free of aliphatic unsaturation, R' is selected from the group consisting of H and $CH_3$ and n is an integral of from 1 to 2 inclusive with a free radical polymerizable monocarboxylic acid. The cyclosilalkoxane is contacted with the free radical polymerizable monocarboxylic acid in the presence of a solvent. The solvent forms an azeotropic mixture with the water formed by the reaction. During the reaction, the azeotropic mixture is continuously removed from the reaction. Also present in the reaction solution is a protonating acid catalyst and a free radical polymerization preventing inhibitor. The process further comprises heating the solution to a temperature which forces the reaction to completion at an accelerated rate. During the reaction sufficient oxygen is supplied to the reaction mixture in order to convert the inhibitor present in the reaction mixture from an inactive to an active form. This process forms a substantially pure free radical polymerizable monomeric unsaturated organosilicone ester in about 3 to about 6 hours.

17 Claims, No Drawings

PREPARATION OF MONOMERIC ORGANOSILICON ESTERS

BACKGROUND OF THE INVENTION

1. Field of the Invention

The invention relates to a novel process for preparing free radical polymerizable monomeric unsaturated organosilicon esters by accelerating the reaction, thereby greatly reducing the reaction time, without polymerizing the free radical polymerizable monocarboxylic acid or the free radical polymerizable monomeric unsaturated esters. The process comprises reacting a cyclosilalkoxane having the general formula:

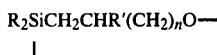

wherein R is a monovalent hydrocarbon radical free of aliphatic unsaturation, R' is selected from the group consisting of H and $CH_3$ and n is an integral of from about 1 to 2 inclusive with a free radical polymerizable monocarboxylic acid. The process steps comprise contacting at least stoichiometric amounts of the cyclosilalkoxane with at least stoichiometric amounts of the free radical polymerizable monocarboxylic acid in the presence of from at least about 25.0 percent by weight, based on the total weight of the solution, of a solvent which will form an azeotrope with water, from about 0.1. percent to about 3.0 percent by weight, based on the total weight of the solution, of a protonating catalytic acid and from about 0.01 percent to about 1.0 percent by weight, based upon the total weight of the solution, of an inhibitor which assists in preventing free radical polymerization of either the final product i.e. the monomeric ester, or the monocarboxylic acid. The process further comprises heating the solution to a temperature of from about 70° C. to about 135° C. while preferably blanketing the reaction with air. The process further comprises continuously removing water, which is produced by the reaction, from the solution during the reaction. This process produces a substantially pure monomeric unsaturated organosilicon ester, in an accelerated manner, without polymerizing the polymerizable monocarboxylic acid or polymerizing the polymerizable organosilicon ester.

PRIOR ART STATEMENT

Morrison and Boyd, Organic Chemistry, Second Edition, Chapter 20, (1966) pp. 666–667 teaches, in pertinent part, that organosilicon esters prepared in the instant invention may be prepared by the following reaction:

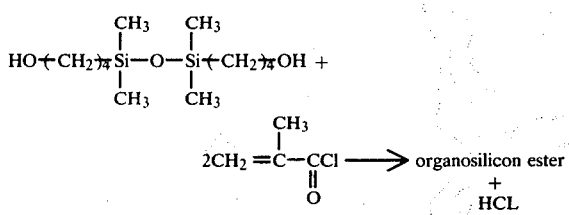

The above reaction is very exothermic. Therefore, it can be a dangerous reaction if the temperature is not controlled very carefully. Also in the above reaction HCl is formed. The HCl is neutralized by using an amine. This reaction is unsuitable for making monomeric organosilicon esters which may be polymerized and used as soft contact lens material since the monomer produced is only about 80 percent pure. In order to use this final product, the product must be processed through several purification steps. The impurities in the final product are attributed to the many side reactions which take place during the main reaction. These side reactions result in many impurities being formed in the end product. Therefore, the novel process of the instant invention was developed in order to produce a purer end product much faster and much safer.

U.S. Pat. No. 2,906,735, in pertinent part, teaches a very slow reaction which produces a product which is also only about 80 percent pure. The general reaction taught in U.S. Pat. No. 2,906,735, in pertinent part, is as follows:

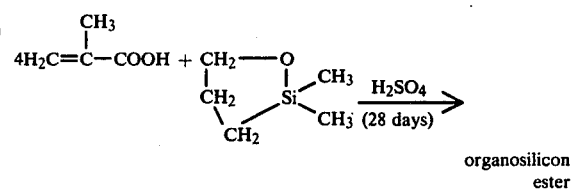

The above reaction involves, in pertinent part, reacting methacrylic acid with a cyclosilalkoxane compound to produce an organosilicon ester. As stated at column 7, line 69 of U.S. Pat. No. 2,906,735 in Table 1, this reaction in order to go to completion using the free radical polymerizable monocarboxylic acid of the instant invention requires 691 hours of reaction time. Therefore, it takes about 28 days in order for the process as taught in U.S. Pat. No. 2,906,735 to produce 80 percent pure organosilicon esters. Again the 80 percent material must go through several purification steps in order to be acceptable for further use. However, most importantly, the reaction time is far too slow. It was discovered that if the temperature was raised in the process as taught by U.S. Pat. No. 2,906,735 the material would polymerize and form a gel, i.e. solidify. This is exemplified in Example I of the instant application. It was also discovered that if inhibitors alone were used, in the processes as taught in U.S. Pat. No. 2,906,735, and the temperature raised, in order to accelerate the reaction, the material would also gel. Therefore, the instant novel process was discovered whereby the temperature could be increased thereby speeding the reaction to completion and at the same time obtaining a much purer product.

None of the above publications or patents teach the instant novel process.

SUMMARY OF THE INVENTION

The present invention involves a process for the preparation, in about 4 to about 6 hours, of monomeric organosilicon esters by reacting a cyclosilalkoxane with a free radical polymerizable monocarboxylic acid in such a way as not to polymerize either the carboxylic acid or the monomeric organosilicon esters. These monomeric organosilicon esters, formed by the instant process, may be reacted with such compounds as octamethylcyclotetrasiloxane to form a long chain siloxane which may be endcapped with activated unsaturated groups. This long chain monomer may then be polymerized i.e. cross-linked, to form three dimensional polymeric networks. These three dimensional polymers may be used to form contact lenses which are optically clear, mechanically strong and which permit the transport of oxygen therethrough.

The preferred embodiment of the instant invention comprises a process comprising reacting a cyclosilalkoxane having the general formula:

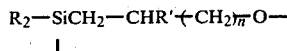

wherein R is a monovalent hydrocarbon radical free of aliphatic unsaturation, R' is selected from the group consisting of H and $CH_3$ and n is an integral of from 1 to 2 inclusive with a free radical polymerizable monocarboxylic acid by contacting at least stoichiometric amounts of the cyclosilalkoxane with at least stoichiometric amounts of the free radical polymerizable monocarboxylic acid in the presence of from at least about 25.0 percent by weight, based on the total weight of the solution, of a solvent which forms an azeotrope with water, from about 0.1 percent to about 3.0 percent by weight, based upon the total weight of the solution, of a protonating catalytic acid and from about 0.01 percent to about 1.0 percent by weight, based on the total weight of the solution, of an inhibitor which assists in preventing free radical polymerization of the monomer and the monocarboxylic acid. Then the solution is heated to about 70° C. to about 135° C. Preferably the reaction is blanketed with air. However, the amount of air required is enough air to supply a sufficient amount of oxygen to the reaction in order to maintain inhibitor activation. The free radicals when formed by the reaction react preferentially with the active inhibitor as opposed to reacting with the available double bonds of the monocarboxylic acid or the organosilicon esters.

The majority of free radicals being formed by the instant reaction are formed thermally. The free radicals formed by the instant process are formed generally by the process as taught by Jerry March "Advanced Organic Chemistry: Reaction, Mechanisms, and Structure," (1968) published by McGraw-Hill Book Co., New York, p. 156. An example of free radical formation in the instant process is as follows:

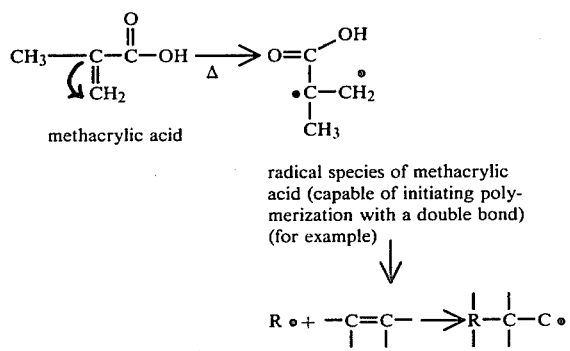

methacrylic acid radical species of methacrylic acid (capable of initiating polymerization with a double bond) (for example)

By the use of the term "inhibitor activation" it is meant herein that the inhibitor obtains the ability to control more free radicals which may be formed during the reaction. When the total amount of inhibitor is added to the reaction a large portion of the inhibitor is in an inactive state i.e. it will not readily react with the free radicals. However, there is a small portion of the inhibitor which is active i.e. will rapidly react with the free radicals, and serves to initially control the free radicals. However, air is added to the reaction in order to supply oxygen in order to convert the inactive inhibitor to the active form i.e. "inhibitor activation." It is believed that the use of a preferred inhibitor such as hydroquinone assists in preventing free radical polymerization. However, after the inhibitor has been used for a certain length of time in the absence of oxygen, it is believed that the active inhibitor loses its ability to control the free radicals. Therefore, it becomes necessary to also introduce air into the reaction, in order to supply oxygen, in order to convert the inactive inhibitor into a usable form i.e. active form. As mentioned, by the active form or usable form, it is meant that the inhibitor obtains the ability to control more free radicals which may be formed by the reaction. For example, when using hydroquinone the active form is quinone and the inactive form is hydroquinone. When air is added to the reaction it supplies oxygen. Therefore, when the reaction contains hydroquinone and oxygen is introduced into the reaction, the hydroquinone is converted to quinone. Quinone is an active inhibitor. Quinone will deactivate the free radicals.

During the reaction, water is continuously removed and monitored from the solution. The stoichiometric amount of water removed from the reaction indicates the completion of the reaction. If the water is not removed from the reaction the reaction will not go to completion. Therefore, the continuous removing of the water is also an important step.

When the term "free radical polymerizable monocarboxylic acid" is used herein, it is meant that the unsaturated group on the monocarboxylic acid is one which has a substituent which facilitates free radical polymerization. If the free radicals formed by the reaction are not controlled then the activated unsaturated groups on the monocarboxylic acid will be polymerized by the free radicals forming undesirable polymers.

When the term "free radical polymerizable monomeric unsaturated" organosilicon ester is used herein, it is meant that the unsaturated group on the ester is one which has a substituent which facilitates free radical polymerization. If the free radicals formed by the reaction are not controlled then the activated unsaturated groups on the ester will be polymerized by the free radicals forming undesirable polymers.

The inhibitors, as mentioned, which are used herein assist in inhibiting free radical polymerization of either the monomeric carboxylic acid or the final product i.e. the monomeric organosilicon esters. Such inhibitors may comprise hydroquinone p-methoxyphenol and 2,6-di-tert-butyl-p-cresol.

As mentioned, the instant process comprising reacting a cyclosilalkoxane with a free radical polymerizable monocarboxylic acid. The cyclosilalkoxane may have the general formula

wherein R is a monovalent hydrocarbon radical free of aliphatic unsaturation, R' is selected from the group consisting of H and $CH_3$ and n is an integral of from 1 to 2 inclusive. Preferably R is a monovalent hydrocarbon radical free of aliphatic unsaturation having from 1 to 6 carbon atoms. Most preferably R is methyl. Preferably R' is hydrogen. Also preferably n is 2. The most preferred cyclosilalkoxane is 1,1-dimethyl-1-sila-2-oxacyclohexane which is represented by the following structure:

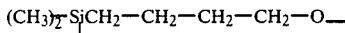

In this reaction the preferred free radical polymerizable monocarboxylic acid has the formula:

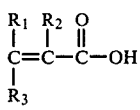

wherein $R_1$, $R_2$ and $R_3$ are selected from the group consisting of hydrogen, monovalent hydrocarbon containing from 1 to 6 atoms and a halogenated hydrocarbon containing from 1 to 6 carbom atoms. The most preferred free radical polymerizable carboxylic acids are acrylic acid and methacrylic acid.

When $R_1$, $R_2$ and $R_3$ equal hydrogen then this is the most preferred free radical polymerizable monocarboxylic acid, i.e. acrylic acid.

When either $R_1$ or $R_2$ or $R_3$ is a monovalent hydrocarbon containing from 1 to 6 carbon atoms, then the preferred acid may be methacrylic acid or cinnamic acid.

When either $R_1$ or $R_2$ or $R_3$ is a halogenated hydrocarbon containing from 1 to 6 carbon atoms, then the preferred acid may be 2-chloropropenoic acid; 3-chloropropenoic acid; 2-fluoropropenoic acid; 2-butenoic acid or 2-trifluoromethyl propenoic acid.

The cyclosilalkoxane is contacted with a free radical polymerizable monocarboxylic acid in at least stoichiometric amounts. The reaction is carried out in the presence of from at least 25.0 percent by weight, based on the total weight of the solution, of a solvent which will form an azeotrope with water since water is produced by the reaction. Forming the azeotrope is desirable because in order for the reaction to continue, the water must be continuously removed from the system. Therefore, the removal can be done by azeotropic distillation. Solvents such as cyclohexane, benzene, hexane, toluene, cyclopentane, heptane, octane, ethylbenzene and xylene may be used. The preferred amount of solvent is from about 40 percent to about 60 percent by weight, based on the total weight of the composition. The preferred solvent is selected from the group consisting of cyclohexane, heptane and benzene. The most preferred is cyclohexane. It is believed that not only does the solvent assist in removing the water from the reaction but the solvent also reduces the tendency of the solution to polymerize.

Also contained in the reaction solution should be from about 0.01 percent to about 1.0 percent by weight, based on the total weight of the solution, of an inhibitor. Preferably this inhibitor is present in amounts from about 0.01 percent to about 0.1 percent by weight, based on the total weight of the solution. As mentioned, this inhibitor assists in inhibiting undesirable free radical reactions. If the activity of these free radicals is not controlled then the solution may polymerize and form a gel, i.e. solidify. In the preferred embodiment the reaction is blanketed with air. Temperatures from about 70° C. to about 135° C. must be maintained in order to accelerate the reaction to completion in 3 to 6 hours. The preferred temperature is from about 80° C. to about 115° C. The most preferred temperature is from about 80° C. to about 90° C.

A strong protonating acid is required as the catalytic acid. These acids are of the type commonly used for transesterification reactions and are well known in the art. Such catalytic acids are of the type taught by Buehler and Pearson, "Survey of Organic Syntheses," Vol. 1, published by John Wiley & Sons Inc. (1970) pp. 814–815. Such preferred acids are sulfuric acid, sulfonic acid, p-toluene sulfonic acid and trifluoromethane sulfonic acid. The catalytic acid is preferred in amounts from about 0.1 percent to about 3.0 percent, most preferably about 0.5 percent by weight, based on the total weight of the solution.

Due to the use of the instant process, the reaction may now be heated up to much higher temperatures than possible from the teachings of the prior art and as a result the reaction is accelerated without polymerizing or gelling. Using known procedures, the reaction would have solidified at these higher temperatures. However, using the instant process, the reaction may be heated up to temperatures as high as 130° C. without solidifying. However, heat around 80° C. is the most preferred. Using this temperature the reaction will go to completion in about 3 to about 6 hours which is a significant advancement in the art. Known reactions which were at room temperature took literally days to go to completion. Then when the reactions did go to completion only an 80 percent pure monomer was obtained.

In its most simplistic form the instant reaction may be illustrated as follows:

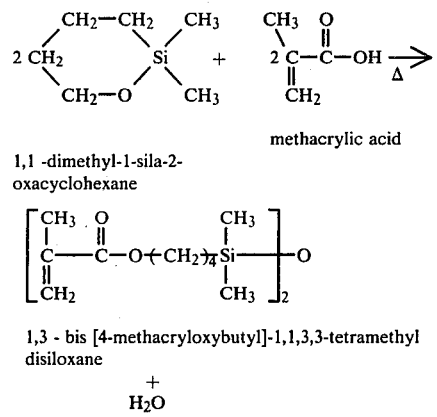

There is no particular limiting ratio of reactants in the defined reaction. As is obvious from the above description, one carboxylic acid group reacts with one silalkoxane unit. Any excess of either reactant can be present. An excess of silalkoxane units results in partial condensation of the silalkoxane to an ester substituted product. An excess of the acid reactant remains as an unreacted component in the reaction mass. Ordinarily, from 1.00 to 1.05 equivalents of carboxy groups for each silalkoxane unit will be a desirable ratio to employ.

The monomeric ester substituted products of the instant process of this invention are of known utility as intermediates for forming polymeric materials for use in making contact lenses. This is taught in U.S. patent application Ser. No. 878,831 filed Feb. 21, 1978, now U.S. Pat. No. 4,190,689.

The monomeric organosilicon esters produced by the instant invention are about 95.0 percent pure. These esters may be further purified by column filtration over activated alumina. This purification step removes the acids e.g. sulfuric acid and methacrylic acid. Also removed by this step is the inhibitor e.g. hydroquinone. The product is now about 98 percent pure. The product may be filtered again over silica gel. This step removes impurities, such as, polar compounds. Then the solvents are removed, for example, by rotary evaporation at reduced pressure or high vacuum distillation. The final product is at least 98 percent pure as determined, for example, by gas chromatography.

The preferred application of the instant monomeric organosilicon esters is as chain terminators in forming polymeric materials. The preferred polymeric material made from the monomeric organosilicon esters of the instant invention is defined as a poly(organosiloxane) monomer $\alpha,\omega$ terminally bonded through divalent hydrocarbon groups to polymerized, free radical polymerizably activated, unsaturated groups forming a homopolymer in a crosslinked network. Contact lenses which may be made from this material are disclosed in U.S. patent application Ser. No. 873,831 filed Feb. 21, 1978, now U.S. Pat. No. 4,190,689.

The following examples are illustrative only and should not be construed as limiting the invention. All parts and percents referred to herein are on a weight basis and all viscosities measured at 25° C. unless otherwise specified.

EXAMPLE #1

71.4 g. 1,1-dimethyl-1-sila-2-oxacyclohexane (0.55 mole), 104.7 g. methacrylic acid (1.22 mole), 5.9 g. hydroquinone, and 6.3 g. concentrated sulfuric acid are weighed into a 1 liter round bottom flask. The mixture is mixed and then allowed to stand for three days at room temperature (22° C.). Then 88.5 g. of benzene is added to the mixture. The flask is then fitted with a Dean-Stark receiver and refluxing condensor. An attempt to remove water from the mixture as a benzene and water azeotrope (b.p. 69° C.) results in gellation of the mixture after 3 hr. reflux and the collection of 7 ml of water.

This example illustrates that if the teachings of U.S. Pat. No. 2,906,735, the most pertinent art, are followed in making the instant monomeric organosilicon esters, the polymerizable reactants polymerize or gel during the azeotropic distillation.

EXAMPLE #2

34.5 g. 1,1-dimethyl-1-sila-2-oxacyclohexane (0.27 mole), 51.1 g. methacrylic acid (0.60), 3.0 g. hydroquinone, and 2.9 g. concentrated sulfuric acid are weighed into a 0.5 liter round bottom flask. The mixture is mixed and then allowed to stand for three days. Then 44 g. of benzene is added to the mixture. The flask is then fitted with a Dean-Stark receiver and condenser. 4.75 g. of water is removed as the water and benzene azeotrope (b.p. 69° C.). The mixture is then transferred to a separatory funnel. The mixture is then washed three times with 70 ml. portions of a saturated water solution of NaHCO3. Then the organic layer is dried with MgSO4 (anhydrous) and filtered. Benzene is removed from the product by rotary evaporation at reduced pressure. A gas chromatography of the product shows it to be 80.1% 1,3-bis (4-methacryloxybutyl) tetramethyl disiloxane with the remaining 19.9% several unidentified by-products.

This example illustrates that if the teachings of U.S. Pat. No. 2,906,735 are followed in making the monomeric organosilicon ester of the instant invention, that a small amount of the final product can be obtained if the azeotropic distillation is stopped after only a few minutes and before polymerization.

The product is 80.1 percent pure. This is unacceptable for most any applications.

EXAMPLE #3

523.8 g. 1,1-dimethyl-1-sila-2-oxacyclohexane (4.0 moles), 304.7 g. acrylic acid (4.2 moles), 1.0 g. hydroquinone, 13.5 ml concentrated sulfuric acid, and 1200 ml cyclohexane are measured into a 3 liter reactor. The mixture is stirred during heating. The mixture is heated with steam (100° C.) and kept under dry air. Water formed during the reaction is removed continuously as the cyclohexane and water azeotrope. After 6 hrs. of heating, 31.9 ml water is collected and heating is stopped. The solution is then column filtered over 1 kg. activated alumina and filtered again over 740 g. grade 12 silica gel. The cyclohexane is removed from the product by rotary evaporation at reduced pressure. 1,3-bis (4-acryloxy butyl) tetramethyl disiloxane is obtained. The product is 98.3% pure by gas chromatography. The identity of the product is confirmed by infrared spectrum and elemental analysis. The analysis results are 55.96% C, 9.26% H, and 13.85% Si.

This example illustrates the instant process. The reaction is completed in 6 hours and the purity is about 98.3 percent.

EXAMPLE #4

510.0 g. 1,1-dimethyl-1-sila-2-oxacyclohexane (4.0 moles), 355.7 g. methacrylic acid (4.2 moles), 1 g. hydroquinone, 28.0 g. sulfuric acid, and 1200 ml toluene are measured into a 3 liter reactor. The mixture is stirred during heating. The mixture is heated with refluxing xylenes (138° C.) and kept under dry air. Water formed during the reaction is removed continuously as the toluene and water azeotrope. After 3 hrs. of water removal, 39.7 ml. of water is collected and heating stopped. The solution is then column filtered over 1 kg. activated alumina and filtered again over 705 g. grade 12 silica gel. The toluene is removed from the product by rotary evaporation at reduced pressure. 1,3-bis (4-methacryloxybutyl) tetramethyl disiloxane is obtained. The product is 98.8% pure by gas chromatography. The identity of the product is confirmed by infrared spectrum.

This example illustrates the instant process. The reaction is completed in 3 hours and the purity is 98.8 percent.

We claim:

1. A process for producing a monomeric organosilicon ester by reacting a cyclosilalkoxane having the general formula

$$R_2SiCH_2CHR'(CH_2)_nO$$

wherein R is a monovalent hydrocarbon radical free of aliphatic unsaturation, R' is selected from the group consisting of H and CH3 and n is an integral of from 1 to 2 inclusive with a free radical polymerizable monocarboxylic acid having the general formula

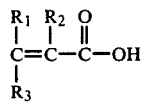

wherein $R_1$, $R_2$ and $R_3$ are selected from the group consisting of hydrogen, monovalent hydrocarbon containing from 1 to 6 carbon atoms and a halogenated hydrocarbon containing from 1 to 6 carbon atoms by (1) contacting at least stoichiometric amounts of the cyclosilalkoxane with at least stoichiometric amounts of the carboxylic acid in the presence of from at least about 25.0 percent by weight, based on the total weight of the solution, of a solvent which forms an azeotrope with water and from about 0.01 percent to about 1.0 percent by weight, based on the total weight of the solution, of a free radical polymerization preventing inhibitor, from about 0.1% to about 3.0% by weight, based on the total weight of the solution, of a protonating catalytic acid, (2) heating said solution of step (1) to a temperature of from about 70° C. to about 135° C. for about 3 hours to about 6 hours while supplying a sufficient amount of air to maintain inhibitor activation, and (3) during the reaction continuously removing from the solution by azeotropic distillation water which is produced by the reaction thereby forming a free radical polymerizable monomeric unsaturated organosilicon ester without polymerizing either the free radical polymerizable monocarboxylic acid or the free radical polymerizable monomeric unsaturated organosilicon ester.

2. The process according to claim 1 wherein R in the cyclosilalkoxane is a monovalent hydrocarbon radical free of aliphatic unsaturation having from 1 to 6 carbon atoms.

3. The process according to claim 2 wherein R in the cyclosilalkoxane is methyl.

4. The process according to claim 1 wherein R' in the cyclosilalkoxane is hydrogen.

5. The process according to claim 1 wherein n in the cyclosilalkoxane is 2.

6. The process according to claim 1 wherein the cyclosilalkoxane is

7. The process according to claim 1 wherein the free radical polymerizable carboxylic acid is acrylic acid.

8. The process according to claim 1 wherein the free radical polymerizable carboxylic acid is methacrylic acid.

9. The process according to claim 1 wherein the solvent of claim 1 is selected from the group consisting of cyclohexane, heptane and benzene.

10. The process according to claim 9 wherein the solvent is cyclohexane.

11. The process according to claim 9 wherein the solvent in step (1) is present in amounts from about 40.0 percent to about 60.0 percent by weight based on the total weight of the solution.

12. The process according to claim 1 wherein the temperature of step (2) is from about 80° C. to about 115° C.

13. The process according to claim 1 wherein the reaction is completed in about 3 hours to about 4 hours.

14. The process according to claim 1 wherein the free radical polymerization preventing inhibitor is selected from the group consisting of hydroquinone, p-methoxyphenol and 1,6-di-tert-butyl-p-cresol.

15. The process according to claim 14 wherein the free radical polymerization inhibitor is hydroquinone.

16. A process comprising reacting (A) a cyclosilalkoxane having the formula

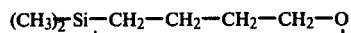

with methacrylic acid by (1) contacting at least stoichiometric amounts of said cyclosilalkoxane with at least stoichiometric amounts of said methacrylic acid in the presence of from about 40 percent to about 60 percent by weight, based on the total weight of the solution, of cyclohexane and from about 0.01 percent to about 0.1 percent by weight, based on the total weight of the solution, of hydroquinone, and from about 0.3 percent to about 0.7 percent by weight, based on the total weight of the solution, of sulfuric acid, (2) heating said solution of step (1) to a temperature of from about 80° C. to about 90° C. while supplying sufficient amount of air to the reaction to maintain inhibitor activation, and (3) during the reaction continuously removing from the solution by azeotropic distillation water which is produced by the reaction thereby forming

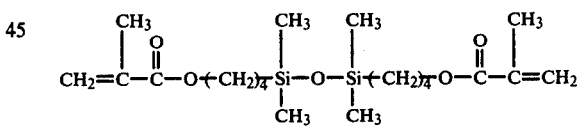

in from about 3 to about 6 hours.

17. The process of claim 16 wherein additional process steps comprise (4) after step (3) purifying the product obtained in step (3) by (2) column filtration over activated alumina (b) then column filtration over silica gel and (c) then solvent evaporation thereby forming a product at least 98 percent pure.

* * * * *

UNITED STATES PATENT AND TRADEMARK OFFICE
CERTIFICATE OF CORRECTION

PATENT NO. : 4,195,030
DATED : March 25, 1980
INVENTOR(S) : William G. Deichert et al It is certified that error appears in the above-identified patent and that said Letters Patent are hereby corrected as shown below:

Col. 1, line 63 under the plus sign delete "HCL" and substitute therefor --- HCl ---;

Col. 5, line 19 after the numeral 6 insert --- carbon ---;

Col. 5, line 20 after the numeral 6 delete "carbom" and insert --- carbon ---;

Col. 6, line 65 after Pat. No. delete "4,190,689" and substitute therefore --- 4,153,641 ---;

Col. 7, line 22 after Ser. No. delete "873,831" and substitute therefor --- 878,831 ---; and Col. 7, line 23 after Pat. No. delete "4,190,689" and substitute therefor --- 4,153,641 ---.

Signed and Sealed this

Twenty-second Day of July 1980

[SEAL]

Attest:

SIDNEY A. DIAMOND

Attesting Officer

Commissioner of Patents and Trademarks